US007835927B2

(12) United States Patent
Schlotterbeck et al.

(10) Patent No.: US 7,835,927 B2
(45) Date of Patent: Nov. 16, 2010

(54) MEDICATION MANAGEMENT SYSTEM

(75) Inventors: David L. Schlotterbeck, Laguna Niguel, CA (US); Stuart E. Rickerson, Rancho Santa Fe, CA (US); Damon J. Coffman, Portland, OR (US); Timothy W. Vanderveen, Poway, CA (US); Bradford A. Lee, Encinitas, CA (US)

(73) Assignee: Carefusion 303, Inc., San Diego, CA (US)

( * ) Notice: Subject to any disclaimer, the term of this patent is extended or adjusted under 35 U.S.C. 154(b) by 2786 days.

(21) Appl. No.: 10/331,034

(22) Filed: Dec. 27, 2002

(65) Prior Publication Data

US 2004/0128162 A1 Jul. 1, 2004

(51) Int. Cl.
*A61B 5/00* (2006.01)
*G06F 19/00* (2006.01)
(52) U.S. Cl. ......................................................... 705/3
(58) Field of Classification Search .................. 705/2–4
See application file for complete search history.

(56) References Cited

U.S. PATENT DOCUMENTS

| | | | |
|---|---|---|---|
| 4,469,481 A | 9/1984 | Kobayashi | |
| 4,696,671 A * | 9/1987 | Epstein et al. | 604/67 |
| 4,857,716 A | 8/1989 | Gombrich et al. | |
| 4,943,279 A | 7/1990 | Samiotes et al. | |
| 4,950,246 A * | 8/1990 | Muller | 604/154 |
| 5,088,981 A * | 2/1992 | Howson et al. | 604/31 |
| 5,100,380 A | 3/1992 | Epstein et al. | |
| 5,104,374 A | 4/1992 | Bishko et al. | |
| 5,154,700 A | 10/1992 | Danby | |
| 5,166,667 A | 11/1992 | Jen | |
| 5,304,126 A | 4/1994 | Epstein et al. | |
| 5,317,506 A | 5/1994 | Coutré et al. | |
| 5,376,070 A | 12/1994 | Purvis et al. | |
| 5,378,231 A | 1/1995 | Johnson et al. | |
| 5,464,392 A | 11/1995 | Epstein et al. | |
| 5,547,470 A | 8/1996 | Johnson et al. | |
| 5,643,212 A | 7/1997 | Coutré et al. | |
| 5,665,065 A | 9/1997 | Colman et al. | |

(Continued)

OTHER PUBLICATIONS

International Search Report, International Application No. PCT/US2003/037324; International Publication No. WO 2004/061745 A3.

*Primary Examiner*—Gerald J. O'Connor
*Assistant Examiner*—Sheetal R Rangrej
(74) *Attorney, Agent, or Firm*—McDermott Will & Emery LLP

(57) ABSTRACT

A system and method for confirming that a medication administration device has been programmed with the correct medication administration parameters. A medical database carrier is used compare medication delivery parameters entered into a medication administration device to institutionally established guidelines or more widely accepted protocols to ensure that the medication is delivered in accordance to those guidelines. The medical database carrier may also be configured to communicate information regarding medication delivery and other patient information between a control system in communication with the care-giving facility's other information systems and a patient specific asset such as an infusion pump. The medical database carrier may be a smart-card, a PDA such as a Palm™ Pilot, laptop computer, pager, mobile phone, or other device capable of storing, processing and communicating information. The system may use either wired or wireless connections to communicate information between the components of the system.

20 Claims, 5 Drawing Sheets

U.S. PATENT DOCUMENTS

| | | | |
|---|---|---|---|
| 5,681,285 A * | 10/1997 | Ford et al. | 604/151 |
| 5,683,367 A | 11/1997 | Jordan et al. | |
| 5,713,856 A | 2/1998 | Eggers et al. | |
| 5,772,635 A | 6/1998 | Dastur et al. | |
| 5,781,442 A | 7/1998 | Engleson et al. | |
| 5,895,371 A | 4/1999 | Levitas et al. | |
| 6,039,251 A * | 3/2000 | Holowko et al. | 235/380 |
| 6,050,940 A | 4/2000 | Braun et al. | |
| 6,055,458 A | 4/2000 | Cochran et al. | |
| 6,055,506 A | 4/2000 | Frasca | |
| RE36,871 E | 9/2000 | Epstein et al. | |

* cited by examiner

MEDICATION MANAGEMENT SYSTEM

BACKGROUND

The present invention relates generally to systems and methods for managing patient care in a health care facility, and more particularly, to systems and methods for integrating and managing information with respect to medical care, medication delivery, asset identification, and verification of drug delivery.

Medication errors, that is, errors that occur in the ordering, dispensing, and administration of medications, regardless of whether those errors cause injury or not, are a significant consideration in the delivery of healthcare in the institutional setting. The Sep. 9, 2002 issue of *Archives of Internal Medicine* reported a study indicating that nearly one in every five doses of medicine given to patients in the typical hospital is a medication error ("Medication Errors Observed in 36 Health Care Facilities"). This study confirms the findings from earlier reports, including the 1999 *Institute of Medicine Report*, which revealed that more than 50,000 deaths in the United States annually are the result of medication errors. Medication errors are the eighth leading cause of death in the United States.

Additionally, adverse drug events ("ADE") defined as injuries involving a drug that require medical intervention, which are a subset of medication errors, represent some of the most serious medication errors, are responsible for a number of patient injuries and death.

Healthcare facilities continually search for ways to reduce the occurrence and severity of medication errors. Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

Several companies are currently marketing or will be marketing hand-held personal digital assistants ("PDA") that are designed to provide drug administration scheduling, drug administration verification, and the electronic documentation of drug administration. These devices are predominantly used to verify administration of oral, intramuscular ("IM"), subcutaneous, and topical drugs and have limited capability in verifying the administration of intravenous ("IV") drugs. One disadvantage of these devices is they are currently incapable of monitoring or receiving data regarding the initial and ongoing infusion parameters of an IV infusion device.

It would be advantageous to have a care management system that combines all the various medication order and administration services of a healthcare facility into an integrated, automated system that checks and documents the delivery of therapeutic and other drugs to the patient. Such a system could help prevent administering an inappropriate medication to a patient by checking the medication itself and the medication delivery parameters against a data base of institutionally established or widely accepted medication administration guidelines. Additionally, the system may compare known allergic reactions and side-effects of the drug against the patient's medical history. The integrated system should also provide doctors, nurses, and other care-givers with updated patient information at the bedside or other point of care, notify the facility's pharmacy when an additional drug is required, or when a scheduled treatment is running behind schedule, and automatically update the healthcare facility's accounting data base and patient medication record each time a medication or other care is given.

In many healthcare facilities, a bracelet device having the patient's identification, such as his or her name printed thereon, is affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a care-giver may miscopy the name or, instead of actually reading the patient's bracelet, rely on memory or a different data source which may be in error. Moreover, manually transferring other information such as parameters for configuring an infusion pump to dispense medication may result in errors that reduce the accuracy and/or effectiveness of drug administration and patient care. This may result in an increased duration of treatment with an attendant increase in cost.

Healthcare facilities continuously strive to provide quality patient care. The possibility of medical errors, such as where the wrong patient receives the wrong drug at the wrong time, in the wrong dosage, or even where the wrong surgery is performed, are a significant concern for all healthcare facilities. Many prescription drugs and injections are identified merely by slips of paper on which the patient's name and identification number have been hand-written by a care-giver who is to administer the treatment. For a variety of reasons, such as the transfer of patients to different beds or different wards and errors in marking the slips of paper, the possibility arises that a patient may be given an incorrect treatment. This could be prevented by using an automated system to verify that the patient is receiving the correct care. Various solutions to these problems have been proposed, such as systems that use bar codes to identify patients and medications, or systems allowing the beside entry of patient data. While these systems have advanced the art significantly, even more comprehensive systems could prove to be of greater value.

Delivery, verification, and control of medication in an institutional setting have traditionally been areas where errors can occur. In a typical healthcare facility, a physician enters an order for a medication for a particular patient. This order may be handled either as a simple prescription slip, or it may be entered into an automated system, such as a physician order entry ("POE") system. The prescription slip or the electronic prescription from the POE system is routed to the pharmacy, where the order is filled. Typically, pharmacies check the physician order against possible allergies of the patient and for possible drug interactions in the case where two or more drugs are prescribed, and also check for contraindications. Depending on the healthcare facility, the medication may be identified and gathered within the pharmacy and placed into a transport carrier for transport to a nurse station. Once at the nurse station, the prescriptions are again checked against the medications that have been identified for delivery to ensure that no errors have occurred.

Typically, medications are delivered to a nurse station in a drug cart or other carrier that allows a certain degree of security to prevent theft or loss of medications. In one example, the drug cart or carrier is divided into a series of drawers or containers, each container holding the prescribed medication for a single patient. To access the medication, the care-giver must enter the appropriate identification to unlock a drawer, door, or container. In other situations, inventories of commonly-used drugs may be placed in a secure cabinet located in an area at or close by a nurse station. This inventory may contain not only topical medications but oral, IM-, and IV-delivered medications as well. Nurse identification and a medication order number are typically required to gain access to the cabinet.

The nurse station receives a listing of drugs to be delivered to patients at intervals throughout the day. A nurse or other care-giver reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Common to all of these systems is the care-giver who delivers the medication. The care-giver is central to the process of verifying that the right medication is given to the right patient in the right dosage at the right time at the point of care. No other person in the facility is situated as well with the requisite experience and training as the care-giver delivering the medication to ensure or verify that the appropriate drug is being given to the appropriate patient.

Such a system works well to verify that patients are receiving the appropriate drug when drugs are delivered orally. But the system may not be capable of thoroughly verifying that the appropriate medication regimen is being delivered to a patient in the case where IV drugs are being delivered. For example, a care-giver may carry an IV bag to a particular patient area, hang the bag, program an infusion pump with appropriate treatment parameters, and begin infusion of the medication. The applicable healthcare facility control system, such as the pharmacy information system, may not know that the patient has received the medication, and if the information is lost somewhere, the possibility exists of medicating the patient twice. Thus, there may be a break in the link of verification that the medication is being properly delivered to the patient if an event occurs resulting in a deviation from the desired treatment parameters.

Moreover, even where the right medication arrives at the right patient for administration, incorrect administration of the medication may occur where the medication is to be administered using an automated or semi-automated administration device, such as an infusion pump, if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment.

Hence what has been recognized as a need, but has heretofore been unavailable, is an integrated system for tracking and controlling patient care and confirming that the correct medication administration parameters are entered into an automatic or semi-automatic medication administration device, and which also may be configured to store the medication administration parameters for later communication to, and integration with, other healthcare facility data bases to achieve safer, more accurate, reliable, efficient, and cost-effective delivery of health care to patients. The invention fulfills this need and others.

SUMMARY OF THE INVENTION

Briefly, and in general terms, the present invention is directed to a new and improved information management system and method capable of monitoring, controlling and validating the administration of medical care in a health care facility.

Generally, the system of the present invention includes a medical database carrier ("MDC") that contains one or more data bases or libraries of information concerning past and present medical administration activities and/or institutional guidelines for appropriate parameters for the administration of various medications. For example, the guidelines may include institutionally established guidelines or limits on drug administration parameters, such as dosage, frequency of administration, and other delivery related information such as, for example, flow rates and infusion durations for programming infusion pumps. Additionally, the guidelines may encompass guidelines for providing drug administration appropriate to particular patient treatment areas having different sets of delivery parameters for similar medications, such as medication administration directed to pediatric, geriatric, or oncology patients. Guidelines may also be included that are directed to particular therapy regimens, such as chemotherapy regimens or regimens for treating chronic infection or pain.

The MDC is used to receive medication administration information from a medication administration device, such as an infusion pump, prior to medication administration, compare that information to institutionally established guidelines for administration of various medications, and provide an alert if any or all of the medication administration information received from the medication administration device falls outside the guidelines. This allows the care-giver administering the medication to correct the administration parameters entered into the medication administration device before medication administration to the patient is begun. If the administration information falls within the guidelines, the care-giver may receive a message generated by the MDC that medication administration may begin. In one embodiment, the medication administration device may be "locked out", that is, electronically prevented from beginning administration of the medication until the medication administration device receives a signal from the MDC that the administration parameters entered into the administration device are appropriate for the medication, and that institutional guidelines for the administration have been met. If the parameters meet these guidelines, the MDC "unlocks" the medication administration device thereby allowing the care-giver to begin medication administration.

In another embodiment, the MDC may maintain a record of the medication administration parameters or information that may be communicated to and incorporated with information in other institutional information systems, such as a pharmacy information system, or healthcare facility information system, or physician order entry system, or a patient specific asset located at a patient's bedside. The information transferred by the MDC is used to validate that the right medication and the parameters of the medication administration record are properly delivered to the right patient.

The MDC in accordance with one aspect of the present invention may be a device having a processor and a memory for storing information or data bases, such as a personal digital assistant ("PDA"), a laptop computer, a desktop computer, a "smart" card, a BLUETOOTH transceiver or similar wireless system, having a processor and memory, or other device capable of communicating with medication administration devices and storing and processing information. The MDC may either be portable, in the sense that the MDC may be moved about the healthcare facility, or the medical database carrier may be primarily stationary and, for example, located at the patient's bedside. At the patient's bedside, the medical database carrier is interfaced to a patient specific asset ("PSA"), such as an infusion pump or similar instrument, or vital signs monitor.

In still another aspect of the invention, information is communicated between the various components of the system using wireless technology. For example, the various components of the system may communicate using a wireless network utilizing communication protocols such as BLUETOOTH™ (IEEE 802.15) or other protocols such as those described in IEEE 802.11, 802.11a, and 802.11b. Communication within the wireless network may utilize radio frequency electromagnetic radiation, infrared radiation or other means for accomplishing wireless communication between network elements.

These and other advantages of the invention will become apparent from the following more detailed description when taken in conjunction with the accompanying drawings of illustrative embodiments.

DETAILED DESCRIPTION OF PREFERRED EMBODIMENTS

The present invention provides a system and method for monitoring, controlling, and tracking the administration of medications in a healthcare facility. Additionally, the present invention also provides for verifying that the right treatment has been given to the right patient in the right manner, in the right amount, at the right time.

Figure 1:
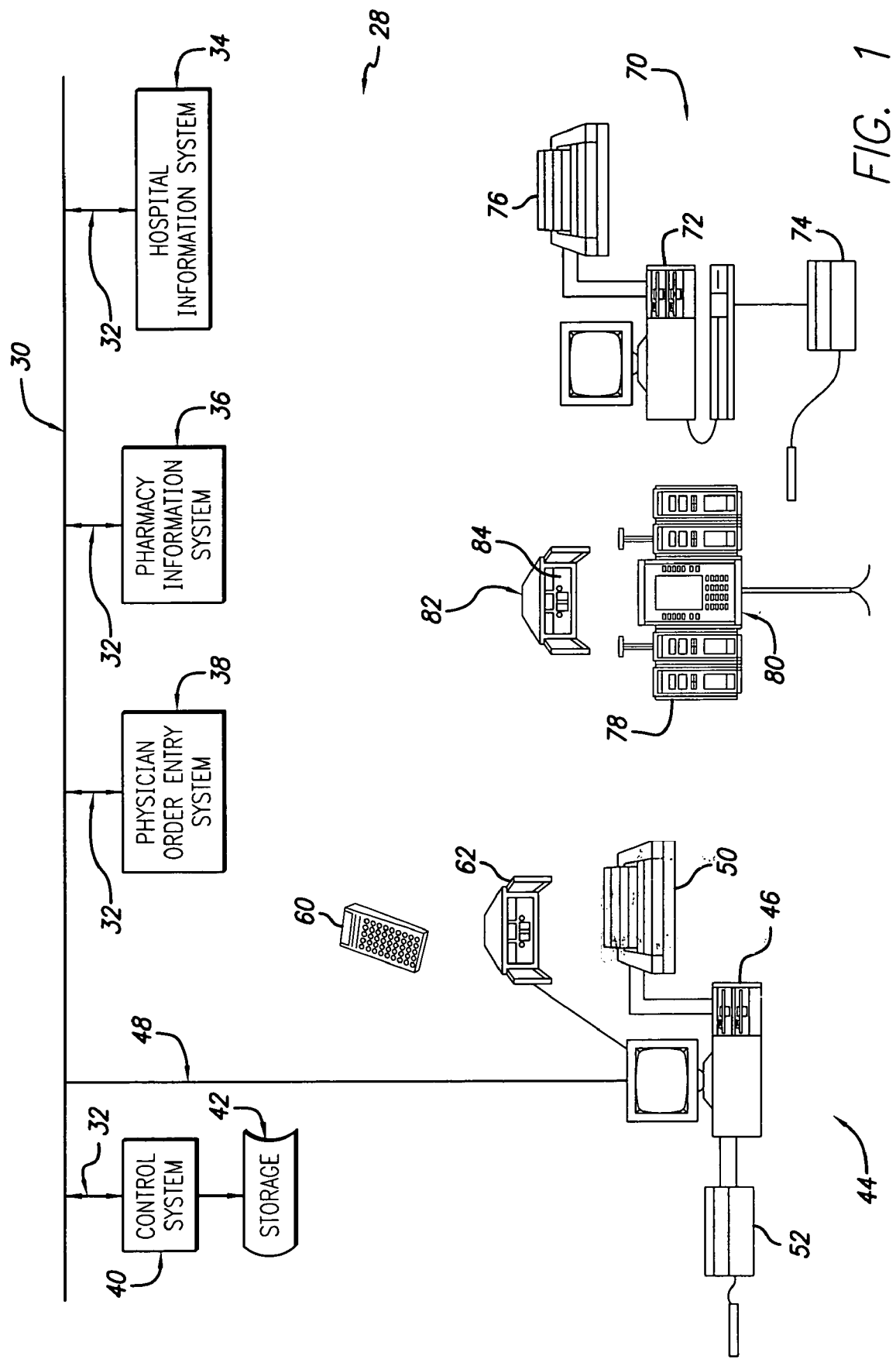
FIG. 1 is a block diagram and graphical representation of a care management system incorporating principles of the present invention and illustrating details of the hardware elements and communications network, and the interconnections of the elements shown.

Referring now to the drawings in which like reference numerals are used to refer to like or corresponding elements among the several figures, there is generally shown in FIG. 1 an integrated, healthcare facility-wide information and care management system 28 in accordance with aspects of the present invention. Various subsystems of a healthcare facility's information management system are connected together by way of a facility communication system 30. The communication system 30 may be, for example, a local area network (LAN), a wide area network (WAN), Internet- or Intranet-based, or some other telecommunications network designed to carry signals allowing communications between the various information systems in the facility. For example, as shown in FIG. 1, the communication system 30 connects, through various interfaces 32, a healthcare facility information system 34, a pharmacy information system 36, a physician order entry system 38, and a control system 40.

The control system 40 in accordance with an aspect of the present invention may include various hardware components, such as a computer, for example an IBM or IBM-compatible personal computer or server, having sufficient mass storage 42, such as local hard drives, CD-ROM, magnetic tape, or other media, and appropriate communication interface capabilities 32 to interconnect with the communication system 30. Although many configurations are possible, in one embodiment, the control system 40 and interface 32 may include hardware such as a data communication router, modem, RF card or other means for communicating with the healthcare facility network 30. The control system 40 also includes a computer program or programs for carrying out various aspects of the present invention, as will be discussed more fully below, and basic operational software, such as a Windows™ operating system, such as Windows™ XP, Windows NT™, or Windows 2000™ or other, distributed by Microsoft, Inc., or other operating program distributed, for example, by Linux, Red Hat, or any other suitable operating system. The operational software will also include various auxiliary programs enabling communications with other hardware or networks, data input and output and report generation and printing, among other functions. While the control system 40 is shown as a separate piece of equipment, it will be understood that the control system 40 and the associated mass storage 42 may also be incorporated into another element, such as an infusion pump or other system.

The communication system 30 may comprise, for example, an Ethernet (IEEE 522.3), a token ring network, or other suitable network topology, utilizing either wire or optical telecommunication cabling. In an alternative embodiment, the communication system 30 may comprise a wireless system, utilizing transmitters and receivers positioned throughout the healthcare facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 1, with the exception that no wires are required to interconnect the various aspects of the system.

In a typical healthcare facility, patient rooms, wards, or areas are typically situated in groups located near a nurse station 44, where the care-givers assigned to care for the patients in the particular area carry out the administrative functions of their duties. Typically, these functions include updating and monitoring the patients' charts, preparation of and administering medication orders, and monitoring and recording any other information deemed necessary by the facility for tracking. There is also usually a room located adjacent the nurse station that is dedicated to storage and/or the preparation of medications to be delivered to patients. This room may contain inventories of commonly used oral, IM, or IV medications. The room may also be used to formulate the contents of infusion bags in accordance with prescribed treatment regimens.

The nurse station 44 will typically include a terminal or computer system 46 connected either directly or through an interface 48 to the communication system 30, allowing users at the nurse station to enter and retrieve patient data or information from other systems, such as the healthcare facility information system 34, the pharmacy information system 36, the physician order entry system 38, or other systems used in the facility. It should be understood that not all users will be provided with access rights to each system. For example, physicians may be able to access the physician order entry system 38 from the nurse station system 44 to enter, edit, or track medication orders, but a care-giver may only be able to view such orders. Moreover, while the present invention is described with reference to the computer system 46 being located at a nurse station 44, the computer system 46 may also be a satellite system that is located anywhere in the care-giving facility where it is convenient or efficient to do so. Such a satellite computer system may be operably connected to the communication system 30 using either a wired or wireless network connection. A printer 50 may also be connected to the nurse station computer system 46 for printing reports, bar codes, labels, or other materials, and a bar code reader 52 may be provided for reading bar codes on medication labels, reports, or other items having bar coded labels provided for identification.

In a different embodiment where RFID tags (RF identification) are used with medications, patients, equipment, or in other ways, the nurse station 44 may also include an interrogator or RFID reader (not shown) for use with the RFID tags.

In accordance with aspects of the present invention, a medication data base carrier ("MDC") 60 including a processor and a memory for storing information is provided to monitor medication parameters or other information used by a care-giver to program a medication administration device to deliver medication to a patient. Various types of information may be stored in the memory of the MDC 60, including data bases containing information about drug interactions and possible contraindications and/or side-effects of medications, and established guidelines for the administration of various medications. For example, the guidelines may include institutionally-established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to a particular patient or to treatment areas having different sets of delivery parameters for similar medications, such as medication administration directed to geriatric, pediatric, and oncology patients. Guidelines may also be included that are directed to particular therapy regimens, such as chemotherapy regimens or regimens for treating chronic infection or pain. The term "data base" or "database" as used herein will be understood by those skilled in the art to be used as is commonly understood. That is, the term refers to a collection of values or information organized, formatted, and stored in such a manner as to be capable of being retrieved and analyzed using an appropriate program contained in software or other form.

In one embodiment of the present invention, the MDC 60 may be interfaced to the nurse station computer system 46 or any other of the information systems of the central system of an institution through a cradle 62 or other docking device that provides a connection between the MDC 60 and the computer system 46. In this embodiment, use of the cradle 62 allows information to flow between the MDC 60 and the nurse computer system 46. This information may then be processed and stored on the computer system 46, or the information may be communicated by the computer system 46 through the interface 48 to various other facility information systems over the communication system 30. In this manner, information from the pharmacy information system 36, for example, may be communicated through the communication system 30, the nurse station 44 computer system 46, and the MDC cradle 62 into the MDC 60. Similarly, information contained within the MDC 60 may be communicated through the MDC cradle 62, the nurse station 44 computer system 46, the interface 48, and the communication system 30 to any of the interconnected systems 34, 36, 38, or 40.

The MDC 60 generally refers to a device that contains medication and/or patient specific information and/or data bases or libraries, including institutionally generated guidelines for the delivery of medication to a patient, as well as drug interaction information or information concerning possible drug side-effects, and that is portable such that it can be carried by a care-giver to and from a patient's bedside. Alternatively, as will be described in more detail below, the MDC 60 may be considered to be relatively stationary in that it is associated with either a particular patient or medication administration device. The MDC 60 may also have a storage capability and technology for interfacing with a computer system or network so that information may be communicated between the MDC 60 and other devices, such as computers, medication administration devices, clinical devices such as vital signs monitoring devices and the like. The MDC may also have a video display screen in color or black and white (mono-color), such as that provided by an LCD or an array of LED's, or other, and a data entry means such as a keyboard, keypad, a screen used for handwriting recognition, or other.

A general concept embodied in the MDC 60 is to provide a system and method wherein medication administration parameters or other information entered into a medication administration device, such as an infusion pump, may be retrieved from the device prior to actual medication administration and compared to information in the data base or data bases stored in the MDC to determine if the entered parameters or information of the administration device fall within institutionally established guidelines for the administration of a particular medication. If the comparison indicates that the parameters or information entered into the medication administration device are appropriate in that they fall within the established guidelines, then an indication to that effect may be provided to the care-giver and the care-giver may then begin medication administration.

Alternatively, if the comparison indicates that one or more parameters or information do not meet the established guidelines, a warning or alert may be provided to the care-giver that one or more parameters or a portion of information has been incorrectly entered into the medication administration device, and that corrective action or an override is required before medication administration can begin. In another embodiment, the medication administration device may be automatically inhibited from starting administration of a medication unless it receives a signal from the MDC 60 that the comparison was favorable, thus providing a fail-safe against incorrect administration of the medication.

Such institutionally established guidelines or more widely accepted protocols for the administration of medications; i.e., medication administration parameters or other information, such as bolus size, maximum dose/hr, maximum continuous dose, volume to be infused, flow rate, and maximum concentration, may be stored in a drug library. The drug library may have preestablished values for infusion parameters that have been generated by the healthcare facility or adopted by the facility. They may comprise the considered "best practices" of the facility and may be updated from time to time. These preestablished values may contain "hard" and "soft" limit values on dosing parameters and other infusion parameters. The facility may set a soft limit for a drug infusion parameter that is a value not normally exceeded in the administration of this drug, but which may be exceeded in exceptional circumstances. The facility may set a hard limit on a drug infusion parameter that is a value not to be exceeded in this facility.

Once the infusion parameter values have been entered into the infusion pump 80 by the care-giver and those values have been communicated to the MDC, the MDC may then enter a verification stage in which it compares each of the selected values against the stored drug library to verify that the entered infusion values are within acceptable ranges. If a value contravenes a hard limit, the MDC 60 may alarm and require a value change before operation of the infusion pump 80 can begin. If the selected infusion parameter value contravenes a soft limit, the MDC 60 may require an acknowledgment from the care-giver that he or she understands that the value entered is outside a soft limit and that this value is nevertheless to remain in force before the infusion can begin. If the acknowledgment is obtained from the care-giver, the MDC may authorize the infusion.

A copy of the drug library in this embodiment may be stored in each MDC 60 of the facility. Alternatively, only select MDC's may have the drug library. In another embodiment, the drug library may be stored elsewhere but accessible by the MDC's. For example, the healthcare facility may have a drug library centrally located in the storage device 42 of the control system 40. In the case where the MDC is in communication with the control system 40, such as through wireless connection or hard-wired connection, the MDC may compare infusion parameters programmed into the PSA 80 against the drug library in the control system.

The MDC 60 typically will also be capable of retrieving medication administration parameters or information from a medication administration device, and storing data or information concerning various transactions in its memory representing the identity and treatment regimens for medications given to a patient, as well as other information, such as care-giver identity, equipment location, patient vital signs information, or any other information sought to be recorded. The MDC 60 may also store data or information concerning primary or secondary validation of previous and/or duplicate transactions of medical treatment information. The display of the MDC may also provide a care-giver with messages or other information, such as warnings or prompts to enter data, related to medication administration. Moreover, the keyboard or other information entry means of the MDC may be used for manually entering information into the MDC for storage in the memory of the MDC.

While specific examples of an MDC 60 are set forth herein, it will be understood that the MDC is meant to include any device that carries out the basic concept of the invention. That is, a device that receives medication administration or treatment information from a medication administration device, such as, for example, but not limited to, an infusion pump or other instrument which performs similar functions, and has a processor capable of comparing the received information to institutionally established medication administration guidelines or other pertinent information or data, such as drug interaction information and/or a library of possible side-effects, and then providing an indication of the result of the comparison to a care-giver before administration of a medication to a patient is begun, will accomplish the aims of the present invention. A particularly advantageous embodiment includes storing information about the medication administration, such as the medication administration or treatment parameters, and/or other information, such as the identity of the patient and care-giver, in the memory of the MDC 60 until the MDC 60 re-establishes a communication connection with the control system 40, whereby the information stored in the memory of the MDC 60 may be communicated to the control system 40 and incorporated into one or more of an institution's information data bases. Updating the data bases provides a verification that the treatment has been rendered, thereby avoiding a duplicate treatment. In this manner, the present invention "closes the loop" ensuring that the right medication has been given in the right manner to the right patient through the rights route at the right time.

For example, consistent with the present invention, the MDC 60 may be embodied in a hand-held "personal digital assistant" ("PDA") such as a Palm™ Pilot or any PDA running either the Palm™ operating system or the Windows™ operating system or other operating system including custom systems, a desktop computer, a notebook computer, or other portable computer system. The MDC may also comprise a Smartcard such as those that are capable of processing and storing data, such as the American Express Bluecard™. The use of such devices is advantageous in that devices having a suitably large memory to accommodate the type of information required by the present invention to monitor and track medication administration information and validate treatment as well as retrieving other patient information, are available and are relatively inexpensive. Thus an MDC may be assigned to each individual patient, or alternatively, to an individual medication administration device, such as an infusion pump, or other clinical device, such as a vital signs monitor. Additionally, such devices are small, compact and easily transportable.

Alternatively, the MDC 60 may be embodied in any device that includes an active embedded processor and a memory capable of storing information. Such an active embedded processor may be even smaller and more portable than a PDA or notebook computer. For the purposes of the present invention, such an active embedded processor includes any device incorporating a microprocessor and allows for input and/or output of information, whether via electrical, radio frequency, magnetic, optical, or other means, wireless or direct contact, and which contains its own power supply. As one example of an active embedded processor in accordance with this invention, such a processor may be attached to or embedded in the packing or container of a medication to be delivered to a patient. Such devices may typically be manufactured no larger than, for example, a postage stamp or business card and yet include, using micro circuitry, enough processing power, information storage, data or information input and output, and power to be suitable for use as a medical database carrier. Such devices are expected to continue to shrink in size in the future. Alternatively, the embedded processor and memory may be integrated into a medication administration device, such as an infusion pump or other device.

Medical database carriers in accordance with the present invention may be either stand alone, as where the MDC comprises a PDA, notebook computer, or a smartcard, or alternatively, the MDC may be attached to or be a built-in part of another piece of equipment or device. For example, a medical database carrier using wireless technology could be incorporated into a medication carrying case or a medication cart. As described previously, a processor may be included in a patient specific asset, such as a medication administration device, that is configured to communicate with an institution's various information systems for receiving information, constituting individual files, or entire data bases, concerning institutionally established guidelines for proper administration of various medications. The processor may also be configured to receive data or treatment information from a medication administration device representing parameters or information entered into the medication administration device by a care-giver, and compare that entered information to the institutional guidelines and determine whether the entered information falls within the guidelines, and provide an indication to the care-giver of the outcome of that comparison. Such a system would be understood to not be strictly portable, but rather stationary, in the sense that the MDC would be associated or mounted to a particular patient specific asset.

In another embodiment, such as where the patient specific asset is modular and includes an advanced programming module ("APM"), such as in the ALARIS Medical Systems, Inc. MEDLEY™ Patient Care System, the APM may include sufficient programming and memory size to perform the function of an MDC. In such case, the APM would be in communication with institutional information systems, such as the pharmacy information system 36, and receive updated information concerning institutional guidelines for medication administration or other patient area or drug specific information to be used to compare with entered medication administration information or parameters before beginning administration of a medication to a patient.

It is not unusual at present to find patient stations 70 having a computer 72 located at patient bedsides in a healthcare facility. Such stations 70 may serve a single patient, or may serve more than one patient, depending on the design and arrangement of the patient area. There may also be a variety of equipment or clinical devices attached to the bedside computer 72. Examples of such devices are a bar code reader 74, a printer 76, patient monitoring equipment (not shown) for monitoring patient vital signs, or other patient specific assets ("PSA") assigned to the patient. Further examples of such PSA's include an infusion device 78 that can form a part of the ALARIS Medical Systems, Inc.'s MEDLEY™ Medication Safety System 80. Attention is directed to U.S. Pat. No. 5,713, 856 entitled "Modular Patient Care System" to Eggers et al., incorporated herein by reference, in which the APM is described as an advanced interface unit "100." In such system, an infusion device "150A" may be mounted to an Advanced Programming Module ("APM"). Other devices, such as a vital signs monitor or monitors, are envisioned as being mountable to the APM also. Other infusion or drug delivery devices and/or patient monitoring equipment such as cardiac or respiratory monitors may also comprise or form a part of the PSA.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside computer 72, or, alternatively, they may be connected, either by wire or wireless system, to the facility communication system 30. Wireless technology, such as RF, IR, or other wireless communication protocols, may be used and "wired" technology establishing a local area network (LAN), Ethernet, or others may be used.

One disadvantage of connecting the equipment or clinical devices directly into the facility communication system 30 or bedside computer 72 is that the PSA may then become immobile and relegated to a single location. This disadvantage is addressed by the present invention in that use of the MDC 60 to transport information such as institutional guidelines (drug library or other) for medication administration to and from a medication administration device or other clinical device or bedside equipment frees the patient device or equipment to be moved from one location to another without requiring changes to a communication network to identify the equipment or device, as is required where the equipment or device is identified as a node on the network.

In accordance with an aspect of the present invention, the PSA 80 may include a communication device 82 used to provide communications between the PSA and the MDC 60. Various forms of such a communication device may be used, depending on the communications technology adopted. For example, where a direct electrical approach is used, a cradle 84 may be used to align the electrical contacts of the MDC with the electrical contacts of the PSA so that a data exchange can occur. In the case where an infrared approach is to be used, the communication device may also take the form of the cradle 84 that physically holds the MDC in a position such that its IR port aligns with the PSA's IR port located in the cradle. When such alignment is provided, data exchange via IR can occur with less possibility of errors and therefore, with greater speed. However, the communication device 82 may also simply take the form of an IR port in the front panel of the PSA 80 and if the data exchange via IR is fast enough, the possibility of errors and retransmission will be reduced.

The MDC cradle 84 may be hardwired to the PSA 80 using the PSA's RS-232 or other communication port. Alternatively, the PSA 80 may include an integrated MDC cradle. Using such an integrated MDC cradle is advantageous in that it eliminates the need for another item of equipment that must be connected to the PSA. Of course, where PSAs having the required MDC cradle technology integrated therein are not available, an external MDC cradle 84 must be used. It will also be understood by those skilled in the art that, where an external MDC cradle 84 is necessary, the MDC cradle 84 may communicate with the PSA 80 using either wired or wireless technology, as described above.

As described previously, one particularly advantageous embodiment of the present invention includes an MDC 60 that is capable of communicating information to and from the PSA 80 and the facility network 30 or control system 40 using wireless technology. For example, the MDC 60 may be understood to include, but is not limited to, communications utilizing optical or infrared transmission, magnetic transmission, or wireless technology where the wireless technology is understood to include methodology such as the BLUE-TOOTH™ technology (IEEE 522.15), standard methodologies such as wireless Internet, WAP or any other proprietary communication scheme using electromagnetic waves instead of wires to connect and communicate between devices. Such wireless communications may also be performed using other wireless networking alternatives, such as those described in the IEEE 522.11x standards. Wireless technologies are designed to create wireless networks allowing devices such as PDA's, cell phones, and personal computers to exchange information at relatively high transmission speeds.

Using BLUE TOOTH™ or equivalent technology, for example, data from a PSA, such as an infusion pump or other medication administration device 80, may be sent by an internal BLUE TOOTH™ communication device 82 taking the form of a radio chip embedded in the PSA 80 to a similarly equipped MDC 60 or, alternatively, to a mobile telephone transmitter/receiver for transmission to a receiver connected to a server system. Using the IEEE 522.11x standards for example, data is transmitted directly to a receiver, which may be wired into a network using Ethernet or other network topology. The MDC of the present invention may be capable of wireless communication using either BLUE TOOTH™ or other technologies (such as those described in IEEE 522.11x), and may be used throughout a care giving facility without the disadvantage of requiring cumbersome hard-wired devices.

One particular mode of operation of the present invention will now be described. A patient entering a healthcare facility is provided with a wrist band, necklace, ankle band, or other band, chain, or device designed to remain affixed to or embedded in the patient during the patient's entire stay in the healthcare facility (the "patient ID"). The patient ID is designed to remain affixed in a manner so that the patient can be identified even if unconscious or otherwise unresponsive. The patient ID holds a patient identifying device that contains specific patient data, such as the patient's name and other information that the facility has determined is important, such as age, allergies, or other vital information. The patient identifying device may comprise a bar code, written information, or an electronic information storage device, such as an RF transponder ("RFID" tag—RF identification tag), that contains the information, or other device affixed to the patient. In the case where the patient identifying device has the needed memory capacity, it may also include the patient's medication administration record ("MAR"). This would allow for traveling documentation and also checks against drug interaction in the MDC.

The RFID tag may be read by a local interrogator or reader such as one contained in each room of the healthcare facility and which is connected with the communication system 30 of the facility. Other approaches are possible such as an RFID tag that must be read at a closer range, for instance, within a few centimeters. In this case, the care-giver may have a PDA that can read the RFID tag of the patient, or the infusion pump may contain an RFID reader. Using a shorter range RFID device can have the advantage of avoiding interference with the RFID tags of other patients, or even the care-giver, who are in the same room as the patient of interest.

It should be noted that RFID tags are becoming less expensive, yet they are becoming more versatile. Some can accept and store new data about the patient in a non-volatile memory and some can derive most, if not all, the power needed for their operation from the radiated energy of the reader. In some cases, a small battery may be used to continually power the storage device or devices in the RFID tag, if needed, while the power needed for responding to an interrogation from a reader can be derived from the transmission of the reader itself.

The bar code, RFID tag, other computing device, or other patient identifying device can be embedded in the wrist band or other band or carrier of the patient so that it remains with the patient at all times. In the case of electronic devices, such as the RFID tag, such a device would be responsive to readers, wireless transmitter/receivers, or antennae located throughout the healthcare facility to provide the identity of the patient along with other information when the patient's identifying device is queried.

Such RFID tags, barcodes, and other technologies useful in identification, may be applied to others and to other things in providing healthcare to patients. For example, physicians, nurses, and other care-givers, as well as others who have access to patients and facilities, may also have an RFID tag that can be read anywhere in the healthcare facility. The medical fluid containers may contain RFID tags having information about the contents of the container as well as the patient for whom they have been prepared, the pharmacist who prepared them, and the physician who prescribed them. The infusion pumps and other healthcare instruments and devices may have RFID tags useful for inventory control. Even though the instruments may be connected to the healthcare facility communication system 30, RFID tags can be useful for manual inventory purposes as well as for other purposes. Their low cost make them attractive as a backup support system.

After the patient is admitted and situated in a bed within the facility, the patient is typically evaluated by a physician and a course of treatment is prescribed. The physician prescribes a course of treatment by preparing an order that may request a series of laboratory tests or the administration of a particular medication to the patient. In some case, the physician prepares the order by filling in a form or writing the order on a slip of paper to be entered into the healthcare facility system for providing care. In other cases, the physician may enter the medication order directly into a physician order entry system 38 (FIG. 1) or may instruct a nurse or other care-giving professional to do so. In yet another case, the physician may use the Internet to forward and enter a prescription for the patient into the pharmacy system. Depending on the arrangement at the healthcare facility, the physician's order or prescription may directly reach a website for the pharmacy 36 or may go to a website for the healthcare facility where it may then be routed to the pharmacy 36.

Pharmacy Internet systems may enable a safer physician medication order process. The pharmacy website may provide the physician with a list of available drugs from which the physician may select. The pharmacy website may contain a drug library having the list of available drugs but may also contain and present to the physician the drug names associated with recommended dosages and dose limits that have been established or adopted by the healthcare facility. In such a case where the physician need only select items from the computer screen rather than having to manually type in drug names and drug administration numbers (such as infusion rates, times, etc.) associated with administration of the medication, a more accurate medication process should result.

If the order is for administration of a particular medication regimen, the order will be transmitted to the facility's pharmacy information system 36. The pharmacy reviews the order, and prepares the medication according to the requirements of the physician. Typically, the pharmacy packages the medication in a container, and a copy of the order, or at a minimum the patient's name, the drug name, and the appropriate treatment parameters are represented on a label or other device that is affixed to the drug container. This information may be represented by a bar code, or it may be stored in a smart label, such as a label having an embedded computer, or in a passive device such as an RFID tag discussed above.

Once the order has been prepared, the order is sent to the nurse station for matching with the appropriate patient. Alternatively, if the medication is for a commonly or routinely prescribed medication, the medication may be included in an inventory of medications that is stored in a secure cabinet adjacent the nurse station. In such a case, the nurse station will receive a list of orders from the pharmacy information system 36 that may be drawn from the inventory adjacent the nurse station. The care-giver will enter a unique identifier at the cabinet to gain access, in accordance with standard practice. The care-giver or other professional assigned the task of gathering medications will then match the orders received from the pharmacy information system 60 to the medications stored in the inventory and pull those medications that are to be delivered to specific patients. These procedures are carried out whether the medication to be delivered is an oral medication, or a medication that is to be delivered intramuscularly or through an infusion.

When the prescribed time for delivery of the medication or medications arrives, the medications are carried to the patient's area and administered to the patient by the care-giver. In the case of drugs to be delivered via infusion, the care-giver hangs the infusion bag and prepares the infusion line, attaches the bag to an infusion pump 78, and sets up the infusion pump to deliver the medication by programming the pump with values for various parameters that are used by the pump to control delivery of the medication to the patient. When the medication delivery parameters are entered into the pump, the pump communicates the entered parameters to the MDC 60 where the parameters are compared by the MDC's processor to institutionally established medication administration guidelines stored in the memory of the MDC. If the outcome of the comparison indicates that the entered parameters are within the guidelines, a message is provided to the care-giver informing the care-giver that the entered parameters are acceptable and that delivery of the medication may begin.

Alternatively, the infusion pump may include a fail-safe circuit or device that prohibits initiation of infusion until the pump 78 receives a signal from the MDC 60 that the entered parameters are within the institutionally established or approved guidelines. Once such a signal is received by the infusion pump, the pump may be started to deliver the medication. Where the comparison is not favorable, such as where one or more parameters fall outside of the institutionally established or approved guidelines, a message to that effect is provided to the care-giver, and the care-giver is prompted to correct the out-of-range parameter or parameters, or enter an override. It will be understood by those skilled in the art that these procedures may be embodied in a portable MDC 60 such as a PDA as described above, or they may be embodied in an MDC that is integrated in or associated with a particular PSA.

With the advent of modern infusion pumps that incorporate microprocessors and storage capability, it has become possible to maintain a record of not only the programmed infusion parameters, but also a log of the treatment as it is given to the patient. Until the present invention, however, there has been no way to ensure that the information gathered by the infusion pump was communicated to a system that could incorporate a record of the infusion into the patient's records stored in any of the healthcare facility's information systems.

Utilizing the present invention, a care-giver gathering or preparing medications to be delivered to patients programs an MDC 60 with the information appropriate to the particular medical treatment regimen that is to be delivered to a patient. Because MDCs are relatively inexpensive, there may be an individual MDC assigned to each patient or PSA 80. As will be discussed below, the MDC 60 provides an instrument for validating the medical transaction to ensure that all information concerning delivery of a medication is retrieved and transferred to the care facility information systems.

In one embodiment, a communication session to transfer medical data base information into an MDC 60 is initiated when connecting the MDC using an appropriate cable or by inserting the MDC 60 into an appropriate slot or cradle which is in operable communication with the healthcare facility's control system 40 via the nurse station computer system 46 and the facility's communication system 30. Alternatively, the MDC 60 may communicate with the control system 40 using a wireless system. As described above, this wireless system may comprise either infrared or RF frequency signals using appropriate communication protocols such as BLUE TOOTH™ or others (such as those described in IEEE 522.11x).

Once a connection has been established between the MDC 60 and the control system 40, the care-giver or other professional, who may also be a systems technician responsible for maintaining the integrity and the currency of the medical data bases stored in the MDC, initiates a download of updated information and data bases into the MDC. Alternatively, communication between the MDC 60 and the control system 40 may be automatically initiated in systems using wireless technology when the MDC comes in close enough proximity to a wireless transmitter/receiver in communication with control system 40. For example, updates of various medical data base files or other information may be stored on the control system 40 in a special "download" or "update" area. When an MDC initiates communication with the control system 40, the control system 40 may be programmed to see if the contents of the "download" or "update" have already been downloaded to the particular MDC. If not, then they are automatically communicated to the MDC; if they have been previously downloaded to the MDC, then no action need be taken.

At the patient location, the information from the MDC 60 is transmitted to the PSA 80 using either wired or wireless technology. In one embodiment, the PSA 80 may be specifically configured to physically receive the MDC 60 to make the connection for transferral of data from the MDC 60 to the PSA. For example, where the MDC is embodied in a smart card or an embedded processor, the communication device 82 of the PSA may include a slot or other device configured to receive the smart card and engage it in such a manner as to allow communication between the PSA 80 and the smart card. Various methods for configuring such a communication connection are well-known in the art and will not be discussed in detail herein, but may include, for example, connector pads in a docking type of arrangement, such as a cradle, or an induction coil capable of interfacing with the smart card to enable communication of information between the smart card and the PSA 80.

In yet another embodiment, the MDC 60 may include a transmitter/receiver configured such that when the MDC comes within a predetermined distance of the PSA 80, a communication link between the MDC 60 and the PSA 80 is automatically established. In one embodiment using a unique identifier associated with a specific PSA 80 to be used to deliver the medication, the MDC 60 may query the PSA 80 to determine if the unique identifier stored in the memory of the MDC 60 matches that of the PSA 80. If the unique identifier stored in the MDC 60 does not match the identifier transmitted to it by the PSA 80, an error signal may be generated alerting the care-giver that the MDC 60 is communicating with the wrong PSA 80, and that the patient may receive the wrong medication.

In the case where a wireless link, such as an RF link, is established between the MDC 60 and PSA 80, data may be both uploaded from the PSA to the MDC and downloaded to the PSA from the MDC, as is discussed below. This wireless connection may permit the care-giver or other person carrying the MDC to be more mobile. As discussed, the MDC 60 may also upload data to and download data from the healthcare facility communication system 30 thereby further permitting the person carrying the MDC to be mobile. Where an entire healthcare facility is configured for wireless transmission and reception with MDC's, greater mobility for persons using the MDC's is presented. As a consequence, data may be transferred more easily and the care-givers may be able to accomplish more tasks in that they do not need to be at a particular station while data transfer occurs.

If the MDC 60 queries the PSA 80 and receives a matching identifier, the MDC 60 may be programmed to prepare to receive medication delivery parameters or other data or information from the PSA 80. The MDC 60 may also query the PSA 80 for historical records stored in the memory of the PSA. In this process, information such as a current key log, error log, vital signs log, infusion delivery log, medication delivery log, transaction identification, maintenance log and other logs and/or other patient data may be transferred from the PSA 80 to the MDC 60.

Additionally, the MDC 60 may remain in communication with the PSA 80 for the duration of the treatment, although the communication link between the MDC 60 and the PSA 80 may also be broken by removing the MDC 60 from the range of the PSA 80 or from the cradle 84. At some time in the future, when the care-giver is making rounds of the patients and determines that the treatment has been completed, communication between the MDC 60 and the PSA 80 may be reestablished. Before the MDC 60 is removed from the proximity of the PSA 80 at the end of the treatment, the care-giver instructs the PSA 80 to transfer desired information, such as that described above, to the MDC 60. The MDC is then removed from the proximity of the PSA 80 or from the cradle 84 attached to the PSA 80 and is carried by the care-giver back to the nurse station computer system 46 or other satellite computer system capable of reading the information stored in the MDC 60.

Once at the nurse station computer system 44, the MDC 60 is inserted into the computer system 46 or MDC cradle 62, depending on the configuration of the equipment, to begin the process of communicating the patient information gathered from the PSA 80 into the storage 42 of the control system 40. Alternatively, particularly in the case where a wireless system is used, the MDC 60 may be activated as it approaches within a predetermined distance of the nurse station computer system 46 or another device, such as a computer system located at a location other than at the nurse station 44 (not shown), or a remotely located transmitter/receiver configured to establish communication with an MDC, to establish a communication connection with the control system 40 over the facility communication system 30.

Figure 2:
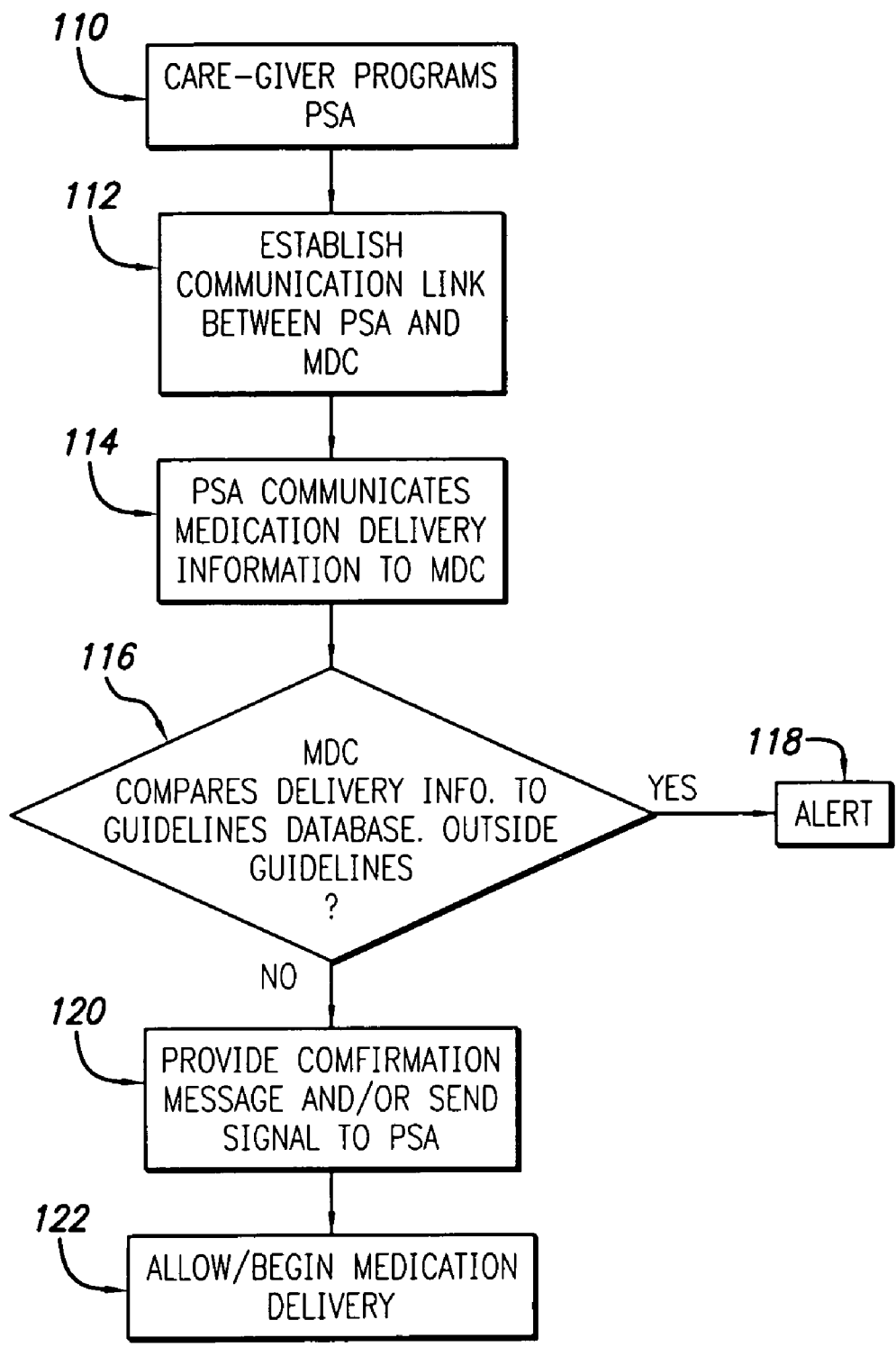
FIG. 2 is functional block diagram illustrating the flow of information between a programmed patient specific asset, such as an infusion pump, and a medication database carrier, and the comparison of the patient specific asset information with guideline data by the medication database carrier, in accordance with aspects of the present invention.

FIG. 2 is a block diagram of one method utilizing the system of the present invention illustrating the use of a medical database carrier 60 (FIG. 1) that is transported by a care-giver to the location where the medication is to be delivered, in communication with a patient specific asset 80 that is to be used to deliver the medication and to retrieve medical transaction information concerning present and past medication delivery from the PSA 80.

The care-giver programs the PSA 80 with the parameters or other information necessary to deliver a particular medication in box 110. A communication link between the PSA 80 and the MDC 60 is established in box 112. This communication link may be a hard wired link, such as a cable or other physical connection, such as a docking port or reader, or it may be wireless. The PSA communicates the medication delivery parameters or other information to the MDC in box 114. The processor of the MDC then compares the communicated medication delivery parameters or other information to institutionally established guidelines or other data or information stored in the memory of the MDC in box 116. If any of the medication delivery parameters or other information are out of range, that is, fall outside of the institutionally established guidelines or other guidelines or limits of the data base or drug library stored in the memory of the MDC, the MDC may provide an alert signal indicating that one or more of the parameters or information are out of range, as shown by box 118. This alert may take the form of a visual, audio, or other message to the care-giver which may be displayed on the MDC, and/or the alert signal may be communicated to the PSA for display by the PSA.

If all of the delivery parameters are within range of the institutionally established guidelines of the drug library, or are acceptable in comparison to other information stored in the memory of the MDC, then the MDC may provide a confirmation message, as in box 120, which may be visual or audio, and may be displayed on the MDC or communicated to the PSA for display. Medication delivery may then be initiated as in box 122. In other embodiments, the message may differ. For example, messages such as "consistent" or "not inconsistent" may be provided thus giving the care-giver further information upon which to base her decision as to starting the pump. These latter messages may indicate that the parameters are "consistent" with the healthcare facility guidelines stored in the MDC.

Alternatively, the PSA may be configured to prevent medication delivery until the PSA receives an appropriate signal from the MDC. In this embodiment, when an acceptable result of the comparison of communicated parameters and information stored in the memory of the MDC has taken place 116, the MDC communicates a signal to the PSA indicating an acceptable comparison 120. Upon receipt of this signal, the PSA "unlocks" and allows initiation of the medication delivery 122. This approach would have particular application to the hard and soft limits feature in the drug library, as discussed above. Should a soft limit be contravened, an input to the MDC from the care-giver would be required before the MDC would unlock the pump. Should a hard limit be contravened, the pump would not be unlocked by the MDC.

Figure 3:
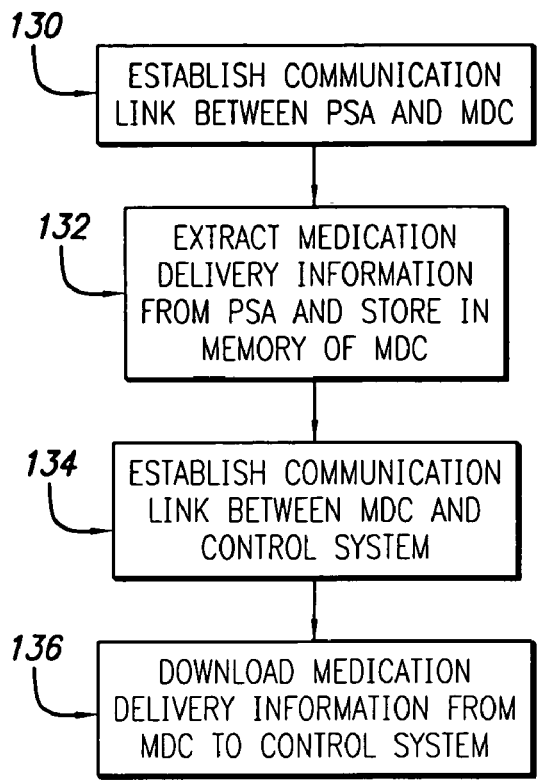
FIG. 3 is a functional block diagram illustrating the flow of information between a programmed patient specific asset ("PSA"), such as an infusion pump, a medication database carrier ("MDC"), and a control system, in accordance with aspects of the present invention, in which information relating to medication deliveries made by the PSA is uploaded to the MDC, which in turn, uploads the information to the control system.

Referring now to FIG. 3, information stored in the PSA 80 related to patient treatments may be communicated to the MDC 60. To carry this method out, a communication link is established between the PSA 80 and the MDC 60 as depicted in box 130, and described above. The processors of the MDC 60 and the PSA 80 cooperate to extract medication delivery information, such as, for example, a current key log, an error log, a vital sign log, infusion delivery log, medication delivery log, transaction ID, maintenance and other logs, and other patient data from a memory of the PSA 80 and store that extracted medication delivery information in the memory of the MDC 60, as shown in box 132. Once the information is stored in the MDC 60, the communication link between the MDC 60 and the PSA 80 may be broken and the MDC 60 may be placed into communication with the control system 40, as illustrated by box 134. Establishing communications with the control system 40 may include physically carrying the MDC 60 to a specified location where the MDC 60 may be interfaced to and establish communication with the control system 40. A hard-wired communications system in which the MDC can communicate with the control system may include an Ethernet system, a LAN system, and others. Alternatively, if the MDC 60 is equipped with appropriate wireless technology, the transport to the control system 40 may become active either upon initiating the transmission by providing the MDC 60 with appropriate commands, or it may be automatically induced using a wireless system. For example, the MDC 60 may be supplied with a transmitter/receiver capable of automatically connecting to the facility communication system 30 to access the control system 40 using a wireless communication protocol such as RF, BLUETOOTH™, or others (for example IEEE 522.11x). Once the communication link is established in box 134, the medication delivery information stored in the memory of the MDC may be uploaded to the control system 40, as shown in box 136 for storage 42 by the control system 40 and processing for various purposes, such as preparing reports or analyzing data, or for updating other healthcare facility records, such as pharmacy and administration records.

Figure 4:
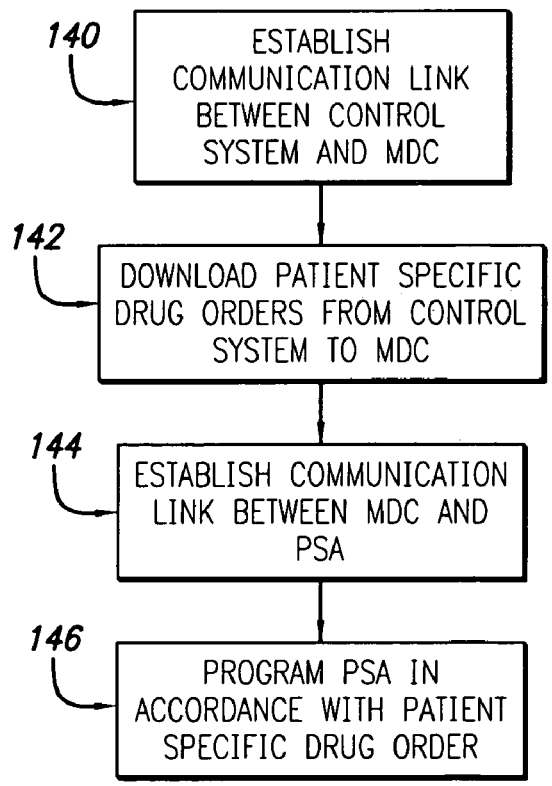
FIG. 4 is a functional block diagram of another embodiment of a care management system wherein the control system downloads drug order information to the MDC which is in turn used to program the PSA accordingly.

Referring now to FIG. 4, another embodiment of the system and method of the present invention is described. In this embodiment, the MDC 60 may be programmed to accept medication delivery information, such as patient specific orders comprising identification information, treatment information, such as flow rates, dosage, and the like, or other information pertaining to the delivery of the medication, and transport that information to a PSA, and program the PSA with that information. To carry out this embodiment, a communication link is established between the central control system 40 and the MDC 60, as depicted in box 140. Patient specific drug orders are then downloaded from the central control system 40 into the memory of the MDC 60, where they are stored, as shown in box 142. The MDC may then be transported to the PSA 80, where a communication link with the PSA is established as shown in box 144, and the patient specific drug order is downloaded into the PSA to program the PSA to deliver the ordered medication in accordance with the patient specific drug order, as depicted in box 146. Because the medication delivery information has come from the central control system 40 and was transferred directly into the PSA by the MDC, the possibilities of an error occurring are decreased or eliminated. However, the process as described above in relation to FIG. 3 may still be undertaken to provide assurance that the medication delivery parameters with which the PSA is now programmed are within the drug library guidelines of the facility. In another embodiment, a drug library may be stored in the PSA and after the PSA has been programmed by the MDC, the PSA compares the delivery parameters with which it has been programmed to those pertinent guidelines of the drug library stored in itself. The PSA may then be enabled for starting the infusion if the comparison was favorable, may indicate that a soft limit was exceeded and require further action by the care-giver before infusion can begin, or indicate that a hard limit was exceeded and a delivery parameter must be changed before infusion can begin.

Figure 5:
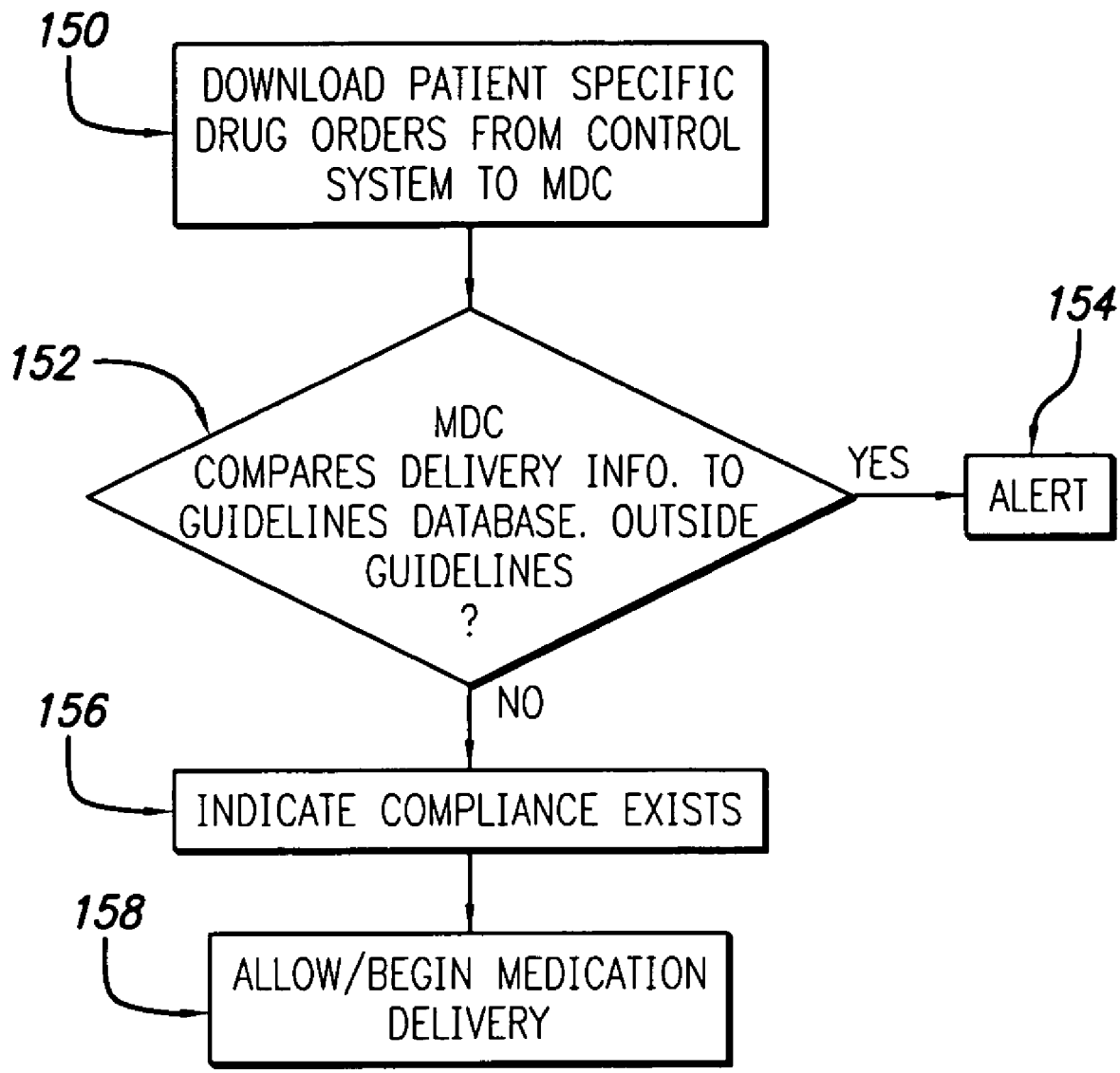
FIG. 5 is also a flow diagram showing the flow of information similar to that of FIG. 4 where a drug order is downloaded from the control system to the MDC, however, the MDC than compares the delivery parameters of the order to a guidelines data base and indicates the results of the comparison.

In an alternative embodiment as shown in FIG. 5, the patient specific drug orders are downloaded from the control system to the MDC in box 150. The processor of the MDC 60, as shown in box 152, compares the downloaded patient specific drug order to institutionally established guidelines or other information stored in the memory of the MDC 60 to determine if the patient specific drug order information is within the guidelines. If the processor determines that one or more aspects of the patient specific drug order do not comply with the institutionally established guidelines, the processor may cause a warning alert, as in box 154, to be provided to a care-giver indicating that correction is necessary. If the comparison indicates that the patient specific drug order complies with the guidelines, then the MDC may provide an indication, such as a visual of auditory signal or message that the order is in compliance with the guidelines and that delivery of the ordered medication may be initiated, as described with reference to box 156 and medication delivery may commence 158.

Figure 6:
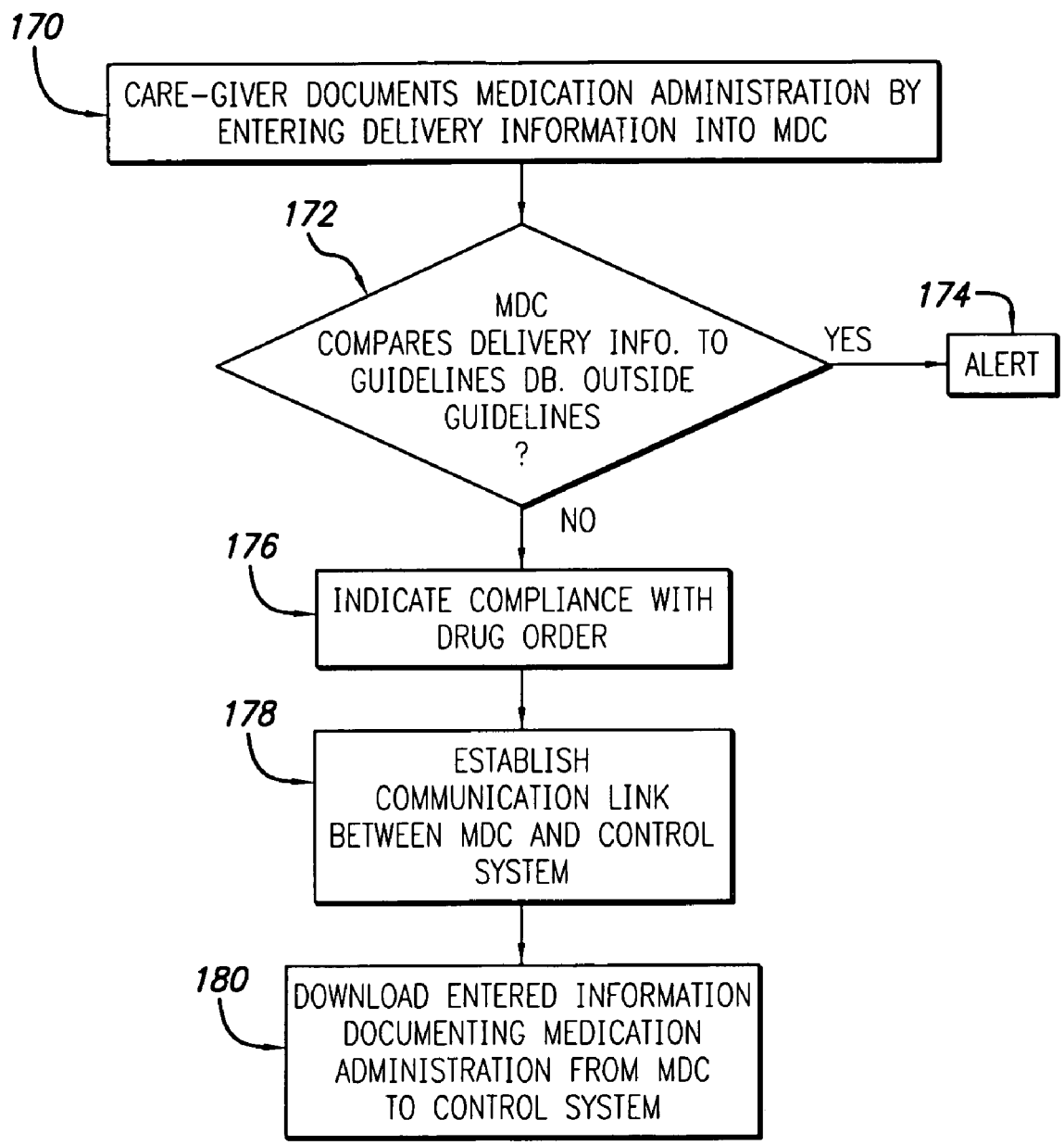
FIG. 6 presents an alternate use of an MDC to compare the actual medication administration to an institution's guidelines and to the actual drug order, and the flow of information from the MDC to the control system.

FIG. 6 depicts yet another embodiment of the present invention wherein the MDC 60 may be used to provide a "second check" of a medication administration and to document the administration of a medication. In this embodiment, as depicted in box 170, a care-giver uses an entry means such as a keyboard to enter information about the administration of a medication, such as delivery time, patient identification, flow rate, dosage, and the like, into the memory of the MDC. The MDC may then compare the entered information to the patient specific drug order stored in the memory of the MDC, as shown in box 172. If the comparison indicates that the medication delivery did not comply with the drug order, a message may be communicated to the care-giver in box 174 indicating that one or more aspects of the medication delivery did not comply with the drug order. If the results of the comparison indicate that the medication administration complied with the drug order, a message to that effect may be provided to the care-giver 176. The care-giver may then transport the MDC to a location where the MDC may establish a communication link to the control system 40, as shown in box 178, and then download the medication administration information to the central control system, as shown in box 180.

In yet a further embodiment concerning manual use of a drug library, the MDC 60 may contain the institutionally established guidelines or widely accepted protocols in a drug library stored in its memory. The care-giver may manually enter the drug name and delivery parameters with which the PSA is programmed into the MDC in a manual check system. The MDC may then make the comparison and indicate a result. The PSA would be under manual control in this embodiment in that the care-giver makes the decision to start or not start the infusion based on the comparison results provided by the MDC. In a related case where the care-giver receives a verbal order from a physician and programs the PSA in accordance with that verbal order, the care-giver may access the PDA for the particular drug prior to starting the infusion to verify that the medication delivery parameters verbally order by the physician are within the drug library limits. The care-giver may start or not start the infusion accordingly.

It should be apparent to those skilled in the art that the MDC may store and transport a wide variety of information useful to the care-givers and care-giving facilities for providing healthcare to patients. For example, the MDC may store in its memory a patient's unique ID, a nurse's or other care-giver's unique ID, specific medication prescribed, and identification of the specific PSA assigned to a specific patient, the time of medication delivery, a current unique transaction ID identifying the current transaction of information between the MDC and the PSA, or the originator of the information such as the healthcare facility information system or the pharmacy information system. Moreover, the MDC, if it includes enough memory, may also be programmed to accept extra pharmacy preparation information as well as extra healthcare facility maintenance or update information. Additionally, other information may be transmitted to and from the MDC as needed by the healthcare facility administration, such as vital signs history and trend information.

As mentioned above, the MDC may take the form of a personal digital assistant such as a Palm Pilot™ device or similar device, but may also take the form of a laptop computer, notebook computer, or other computing devices. In the case where the MDC is embodied in a personal digital assistant, the size and weight of the MDC are such that the care-giver may easily carry the MDC in a pocket.

In establishing the institutional guidelines and preparing the drug library with the hard and soft limits, a computer program configured to accept user inputs related to pump operating parameter limits specific to the drugs contained in the library and to generate a data base from those user inputs is provided. This program may run on Windows™ based computer systems or others, and the data base created may be stored in the patient specific asset, such as an infusion pump, or the MDC, for use in verifying that the delivery parameters programmed into the patient specific asset are within limits.

While the PSA was primarily described in terms of an infusion pump, the PSA, as described above, may also be a vital signs monitor or other clinical device interacting with a patient. For example, the PSA may also be a patient feeding device.

Furthermore, the "facility" communication system 30 as mentioned above numerous times is not meant to be taken in a limited sense. Such a communication system may encompass an entire healthcare facility or may be located only in a small area of the healthcare facility. It may also include a communication system in a healthcare facility other than a hospital and may have application to an alternate care facility, such as a patient's home. The above embodiments are described for exemplary purposes only. The word "caregiver" is intended to be used in its broadest sense and is meant to include nurses as well as others who provide care to patients.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a healthcare facility environment, it will be understood that the system and method may be useful in other environments as well, such as outpatient clinics and other environments where care is delivered to a patient.

While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. A system for use with an infusion pump for reducing the possibility of medication errors, the infusion pump being capable of being programmed with pumping parameters, the system comprising:
   a first program configured to accept user inputs related to pump operating parameter limits and to generate a data base from those user inputs; and
   a second program located in an infusion pump configured to:
   receive the pump parameter data base generated by the first program;
   compare pumping parameters programmed into the infusion pump by an operator with the data base; and
   monitor the comparison and if the comparison exceeds the limits established in the data base, provide an indication to a pump operator that the programmed pumping parameter is outside the limits in the data base.

2. The system of claim 1 wherein the first program is configured to be executed on a first computer separate from the infusion pump.

3. The system of claim 1 wherein the first program includes names of drugs and associates multiple pumping parameters with at least one of said drugs.

4. The system of claim 1 wherein the second program causes the pump to display a visual indication to the operator that the programmed pumping parameter is outside the limits selected by the facility in which the pump is located.

5. The system of claim 4 wherein the indication presented to the operator further queries the operator as to whether the operator desires to override the indication.

6. The system of claim 1 wherein the second program creates a log of all comparisons that exceed the limits established in the data base.

7. The system of claim 1 wherein:
   the first program comprises an editor subprogram that enables an operator of a first computer to generate a data base of pumping parameters associated with multiple drugs; and
   the first program is also configured to have a second subprogram that, when commanded, will install the data base in a selected infusion pump.

8. The system of claim 7 wherein the infusion pump comprises a processor that automatically compares the programmed pumping parameters to the data base that has been installed in the pump and immediately presents an indication of a program parameter that is outside the data base as it is detected.

9. The system of claim 7 wherein the infusion pump comprises a processor that automatically compares the programmed pumping parameters to the data base that has been installed in the pump one-by-one as they are entered into the pump and presents an indication of a program parameter that is outside the data base if such is detected.

10. The system according to claim 1 wherein the second program is further configured to:
    prevent an operator from initiating pumping action of the pump once an indication of a parameter being outside the data base is presented until; and
    permitting an operator to initiate pumping action of the pump once the operator has either changed the outside parameter to be within the limits in the data base or indicated that the operator desires to proceed regardless of the out of limits parameter.

11. A system for use with a patient medical device, the device having specific operating data associated with it, the system comprising:
    a first processor configured to accept user inputs related to operating data limits associated with the medical device and to generate a data base from those user inputs; and
    a second processor configured to:
    receive the data base generated by the first processor;
    compare the actual operating data of the medical device with the data base limits; and
    monitor the comparison and if the comparison shows that actual operating data of the medical device exceed the limits established in the data base, provide an indication the operating data of the medical device are outside the limits in the data base.

12. The system of claim 11 wherein the first processor is separate from the medical device.

13. The system of claim 11 wherein the first processor includes names of drugs and associates multiple medical device operating parameters with at least one of said drugs.

14. The system of claim 11 wherein the second processor causes the medical device to display a visual indication that the operating data are outside the limits selected by the facility in which the medical device is located.

15. The system of claim 14 wherein the visual indication displayed further queries an operator as to whether the operator desires to override the indication.

16. The system of claim 11 wherein the second processor creates a log of all comparisons that exceed the limits established in the data base.

17. The system of claim 11 wherein:
the first processor comprises an editor subprogram that enables an operator to generate a data base of operating parameters associated with multiple drugs; and
the first processor is also configured to have a second subprogram that, when commanded, will install the data base in a selected medical device.

18. The system of claim 11 wherein the medical device comprises a third processor that automatically compares the operating data one-by-one as they are entered into the medical device to the data base that has been installed in the medical device and immediately presents an indication of the programmed data that is outside the data base as it is detected.

19. The system according to claim 11 wherein the second processor is further configured to:
prevent-an operator from initiating operation of the medical device once an indication of data being outside the data base is presented; and
permitting an operator to operate the medical device once the operator has either changed the outside data to be within the limits in the data base or indicated that the operator desires to proceed regardless of the out of limits data.

20. The system according to claim 11 wherein the first and second processor are a single processor that is configured to:
accept user inputs related to operating data limits associated with the medical device and to generate a data base from those user inputs;
compare the actual operating data of the medical device with the data base limits; and
monitor the comparison and if the comparison shows that actual operating data of the medical device exceed the limits established in the data base, provide an indication that the operating data of the medical device are outside the limits in the data base.

* * * * *

(12) EX PARTE REEXAMINATION CERTIFICATE (9793rd)
United States Patent
Schlotterbeck et al.

(10) Number: US 7,835,927 C1
(45) Certificate Issued: Aug. 12, 2013

(54) MEDICATION MANAGEMENT SYSTEM

(75) Inventors: David L. Schlotterbeck, Laguna Niguel, CA (US); Stuart E. Rickerson, Rancho Santa Fe, CA (US); Damon J. Coffman, Portland, OR (US); Timothy W. Vanderveen, Poway, CA (US); Bradford A. Lee, Encinitas, CA (US)

(73) Assignee: Carefusion 303, Inc., San Diego, CA (US)

Reexamination Request:
No. 90/011,697, May 18, 2011
No. 90/009,912, Jun. 6, 2011

Reexamination Certificate for:
Patent No.: 7,835,927
Issued: Nov. 16, 2010
Appl. No.: 10/331,034
Filed: Dec. 27, 2002

(51) Int. Cl.
*A61B 5/00* (2006.01)
*G06F 19/00* (2011.01)

(52) U.S. Cl.
USPC .............................................................. 705/3

(58) Field of Classification Search
USPC .............................................................. 705/3
See application file for complete search history.

(56) References Cited

To view the complete listing of prior art documents cited during the proceedings for Reexamination Control Numbers 90/011,697 and 90/009,912, please refer to the USPTO's public Patent Application Information Retrieval (PAIR) system under the Display References tab.

*Primary Examiner* — Jimmy G. Foster

(57) ABSTRACT

A system and method for confirming that a medication administration device has been programmed with the correct medication administration parameters. A medical database carrier is used compare medication delivery parameters entered into a medication administration device to institutionally established guidelines or more widely accepted protocols to ensure that the medication is delivered in accordance to those guidelines. The medical database carrier may also be configured to communicate information regarding medication delivery and other patient information between a control system in communication with the care-giving facility's other information systems and a patient specific asset such as an infusion pump. The medical database carrier may be a smart-card, a PDA such as a Palm™ Pilot, laptop computer, pager, mobile phone, or other device capable of storing, processing and communicating information. The system may use either wired or wireless connections to communicate information between the components of the system.

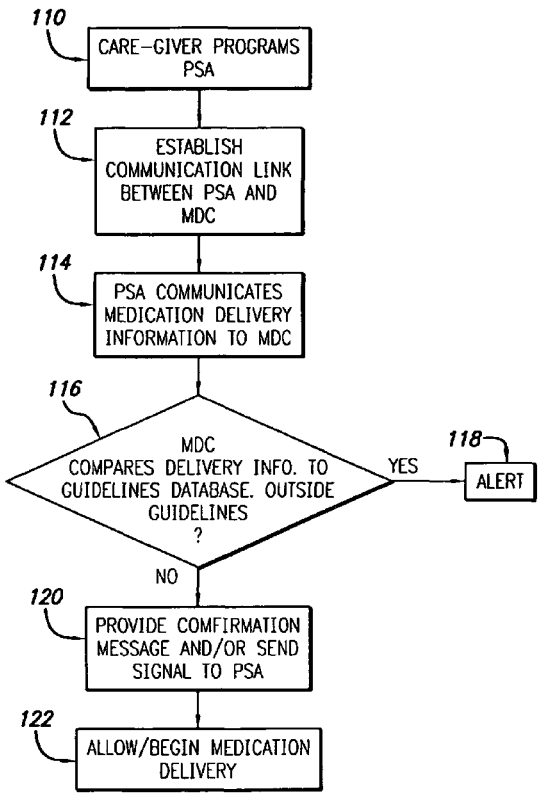

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*